United States Patent
Sato et al.

(10) Patent No.: US 10,912,787 B2
(45) Date of Patent: Feb. 9, 2021

(54) USE OF N-ACETYLGLUCOSAMINE AND DERIVATIVES THEREOF TO TREAT MUSCLE DISORDERS

(71) Applicant: PUREPHARM INC., Toronto (CA)

(72) Inventors: Sachiko Sato, Saint-Augustin-de-Desmaures (CA); Masahiko Sato, Saint-Augustin-de-Desmaures (CA); Ann Rancourt, Levis (CA)

(73) Assignee: PurePharm, Inc., Toronto (CA)

( * ) Notice: Subject to any disclaimer, the term of this patent is extended or adjusted under 35 U.S.C. 154(b) by 118 days.

(21) Appl. No.: 16/045,250

(22) Filed: Jul. 25, 2018

(65) Prior Publication Data

US 2018/0369261 A1    Dec. 27, 2018

(30) Foreign Application Priority Data

May 26, 2017  (CA) .................................... 2968160

(51) Int. Cl.
*A61K 31/7008* (2006.01)
*A61P 21/00* (2006.01)

(52) U.S. Cl.
CPC .......... *A61K 31/7008* (2013.01); *A61P 21/00* (2018.01)

(58) Field of Classification Search
None
See application file for complete search history.

(56) References Cited

U.S. PATENT DOCUMENTS 4,870,061 A * 9/1989 Speck ................ A61K 31/7004
                                                        514/62
2013/0287853 A1* 10/2013 Vournakis .......... A61K 48/0075
                                                        424/489

OTHER PUBLICATIONS

Leung, D. G., & Wagner, K. R. (2013). Therapeutic advances in muscular dystrophy. Annals of neurology, 74(3), 404-411. (Year: 2013).*
Strassburg, S., Springer, J., & Anker, S. D. (2005). Muscle wasting in cardiac cachexia. The international journal of biochemistry & cell biology, 37(10), 1938-1947. (Year: 2005).*
Bossola, M., Pacelli, F., & Doglietto, G. B. (2007). Novel treatments for cancer cachexia. Expert opinion on investigational drugs, 16 (8), 1241-1253. (Year: 2007).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
U.S. Appl. No. 16/295,448, filed Mar. 7, 2019.
U.S. Appl. No. 62/640,431, filed Mar. 8, 2018.

* cited by examiner

*Primary Examiner* — Dale R Miller
(74) *Attorney, Agent, or Firm* — Colleen M. Schaller; Howson & Howson LLP

(57) ABSTRACT

Methods of preventing or delaying the weakening of as well as improving the strengthening of muscles includes the step of providing an effective amount or dose of N-acetylglucosamine (GlcNAc), related saccharides, or combinations thereof both to improve myogenesis.

7 Claims, 2 Drawing Sheets

Fig. 1
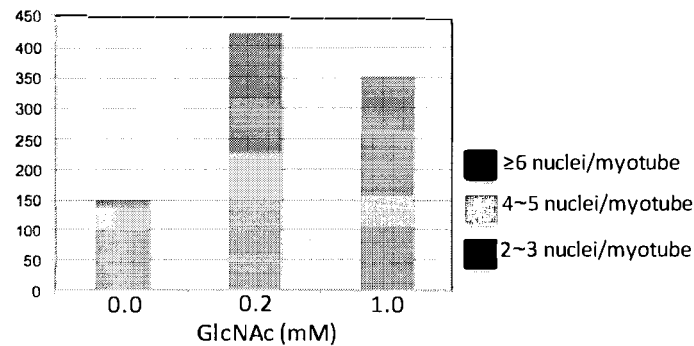
Fig. 2A    Fig. 2B
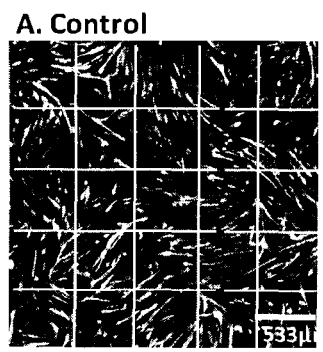 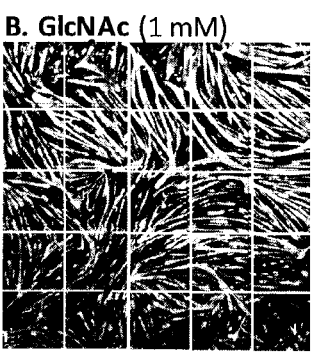
Fig. 3
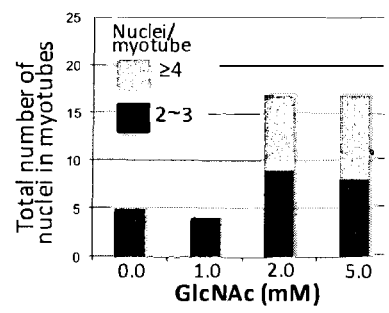

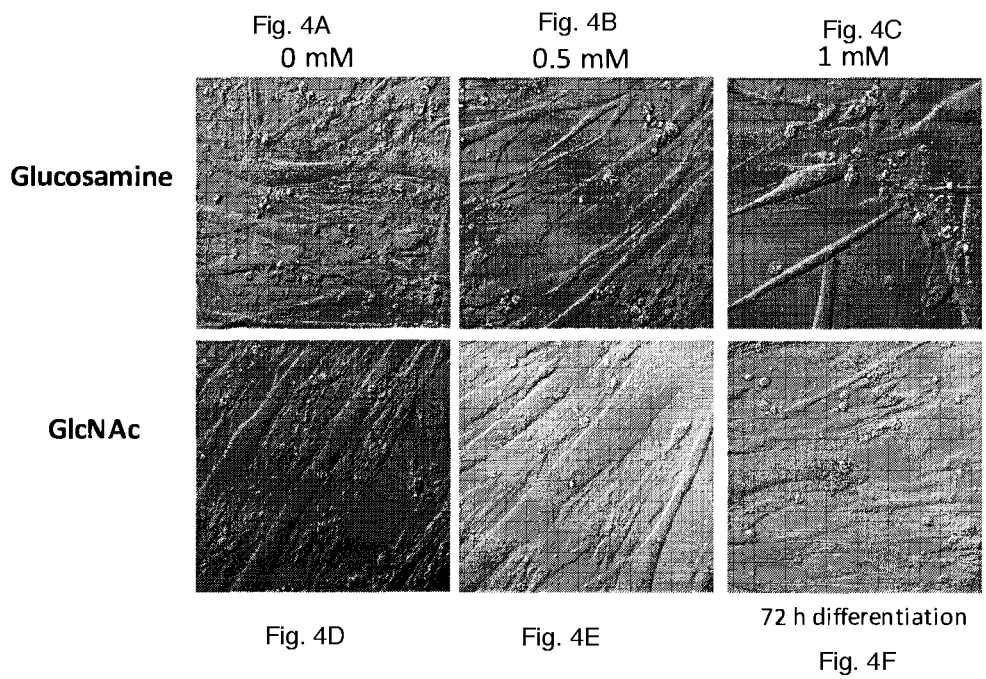
Fig. 4A 0 mM
Fig. 4B 0.5 mM
Fig. 4C 1 mM
Glucosamine
GlcNAc
Fig. 4D
Fig. 4E
72 h differentiation
Fig. 4F
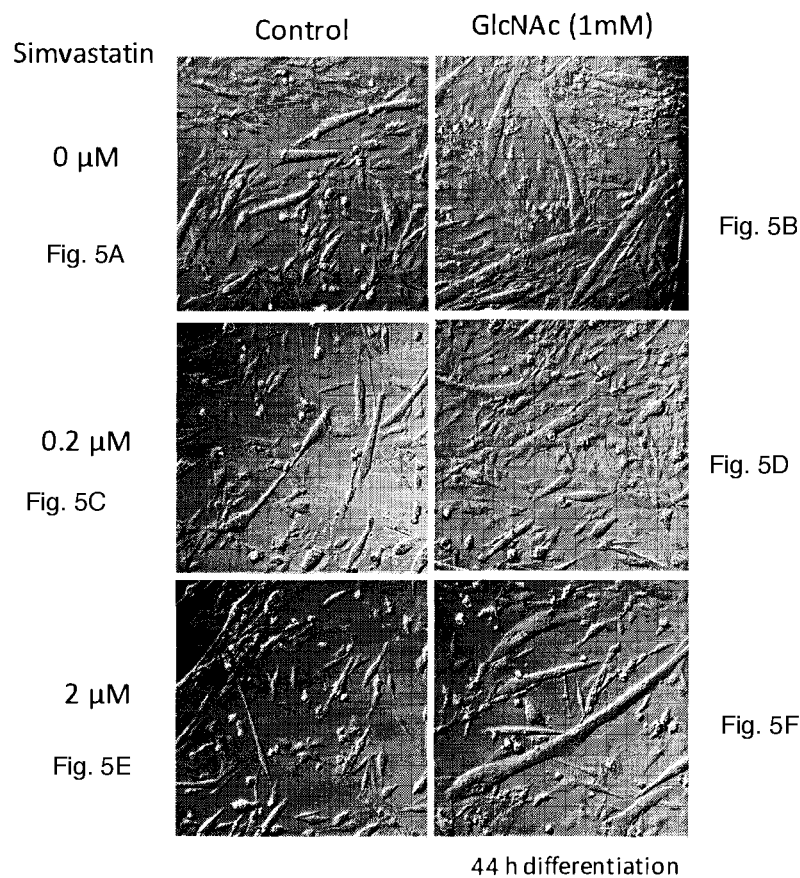
Simvastatin
Control
GlcNAc (1mM)
0 μM
Fig. 5A
Fig. 5B
0.2 μM
Fig. 5C
Fig. 5D
2 μM
Fig. 5E
Fig. 5F
44 h differentiation

USE OF N-ACETYLGLUCOSAMINE AND DERIVATIVES THEREOF TO TREAT MUSCLE DISORDERS

CROSS-REFERENCE TO RELATED APPLICATIONS

This application incorporates by reference and claims the benefit of priority to Canadian Patent Application 2,968,160 filed on May 26, 2017.

BACKGROUND OF THE INVENTION

The present invention relates to the field of medicine. More particularly, it relates to methods of treating muscle injuries, disorders and muscle atrophy using N-acetylglucosamine or related saccharides that induce the similar effect with N-acetylglucosamine.

The adult skeletal muscle tissue is composed by specialized cells called myofibers. In normal muscle, sarcolemma (muscle membrane) is firmly attached to the basal lamina. Accordingly, repeated or unaccustomed eccentric contractions, which are required in normal life activity, do not cause major muscle injury. However, when the level of use, metabolic load or stress on a myofibers reaches a certain level, the fiber breaks, leading to degeneration of the fiber, which is replaced with a new muscle fiber through the process of regeneration (myogenesis). After a muscle injury, the quiescent resident population of myogenic precursor satellite cells that resides proximal to the injured fiber begins to proliferate and to differentiate into myoblasts. These mononuclear cells proliferate to create myocytes, which fuse with each other to form multinucleated myotubes or fuse with existing myofibers. Finally, myotubes align to form the muscle fibers. The process of myogenesis is regulated by many internal and external factors.

In some individuals, this process of myogenesis is either impaired or chronically activated due to intrinsic muscle weakness, continuous muscle injury and degeneration, which are associated with muscle diseases. In Europe, over 15 million people suffer from muscle diseases that inevitably progress to loss or atrophy of muscle tissue. Many of these diseases are genetic and are the result of various medical conditions such as hospitalization or prolonged immobilization. Medications such as statins (a cholesterol lowering drug) may also induce muscular injury or weakness. In addition, skeletal muscle atrophy results from aging, cancer-induced cachexia and this atrophy is the main cause of the fragility of the elderly. Sarcopenia and muscular dystrophy have similar characteristics, including fibrosis, a wide distribution of fiber size, and central. There are no available cures for this muscle loss.

The muscular dystrophy (MD) is a group of heterogeneous genetic neuromuscular diseases, which are characterized by progressive degeneration and weakness of skeletal muscle. Myotonic dystrophy type 1 (DM1) is the most common form of muscular dystrophy developing in adulthood. DM1 is a multisystem disorder that affects the skeletal muscle, the eye, the heart, the endocrine system, and the central nervous system. The progressive muscle degeneration occurs and the myogenesis is generally impaired, which leads to the depletion of the satellite cells. DM1 is caused by expansion of a CTG trinucleotide repeat in the noncoding region DMPK (dystrophia myotonica protein kinase), which encodes an enzyme, a serine/threonine kinase. An expansion of this volatile repeat over 50 results in DM1 dystrophy symptoms having an increasing severity corresponding to an increasing numbers of repetitions. Muscle tissue of DM1 patients is histologically abnormal. Features include the variability in size of the fibers, fibrosis, rows of inner cores, annular fibers, sarcoplasmic masses, and an increase in intrafusal muscle fibers. In patients having DM1, the adult muscle regeneration is continuously activated due to frequent muscle injury, leading to deplete muscle stem cells.

The most common form of muscular dystrophy in childhood with an incident of 1:5000 is Duchenne muscular dystrophy (DMD), a severe X-linked recessive disorder. Individuals affected with this dystrophy suffer from progressive muscle wasting and severe muscle degeneration, which becomes evident before 4 years old, need assisted ventilation before the age of 20 and have short lives. Their muscle lacks a protein called dystrophin, an essential linker that connects the intracellular cytoskeleton of myofibers to the extracellular matrix. Consequently, the muscle membrane does not tolerate repetitive contraction, which leads to progressive muscle degeneration.

In normal muscle, sarcolemma (muscle membrane) is firmly attached to the basal lamina. Accordingly, repeated or unaccustomed eccentric contractions, which are required in normal life activity, do not cause major muscle injury. However, in the muscle of MD patients, this type of daily contractions results in fiber degeneration, because the sarcolemma is not properly fixed to the basal lamina. The fiber degeneration is then counterbalanced by myogenesis at the expense of satellite cells. Therefore, the frequent degeneration of muscle fiber in MD patients eventually overwhelms the capacity of myogenesis.

Very few if any treatment except treatment with corticosteroids is currently available in the market to prevent or delay either the onset or the progression of muscular dystrophy or muscular atrophy of individuals who do not suffer from muscular dystrophy. Similarly, there is no treatment to enhance the muscular regeneration. In the era of genomics and stem cell research, development of therapies for genetic diseases is dominated by innovative yet expensive gene or stem cell-based therapies. As muscles constitute 40%-45% of human body mass, those future therapies will also have to overcome the hurdle of delivery efficiency. Thus, gene- or cell-specific therapy will take at least another decade or more to become a standard therapeutic option for muscular dystrophies.

Accordingly, there is a need to improve the health of muscle tissues, to strengthen the muscle membranes attachment to the basal lamina, which protects muscle against contraction and also to increase the efficiency of muscle regeneration thereby offering an option to delay the disease progression.

SUMMARY OF THE INVENTION

Disclosed herein are methods of treating muscular disorders, including but not limited to muscular dystrophy, muscle injury, muscle atrophy, and muscle loss. In some examples, the method includes administering to the subject with muscular disorders an effective amount of an agent that alters biological activity of one or more molecule(s) associated with muscle regeneration and/or health and/or modify post-translational modification of those proteins thereby treating the muscular disorders and delaying the onset of muscular atrophy and muscular dystrophy.

The present invention provides methods of preventing or delaying the weakening of as well as improving the strengthening of muscles including the step of providing an effective amount or dose of N-acetylglucosamine (GlcNAc), related saccharides, or combinations thereof both to improve myogenesis. For example, some embodiments provide methods of improving muscular health and symptoms of muscular disorders, including muscular dystrophy, muscle injury, muscle atrophy, and muscle loss. The present invention provides methods of improving muscular health, such as enhancing muscle maintenance, regeneration (myogenesis), or repair of injured muscle.

Muscular dystrophy treatment or delay onset: GlcNAc, the related saccharides, or combinations thereof optimize the muscle environment for glycosylation of proteins that are critically involved in the maintenance, regeneration and health of muscles. The treatment according to the present application is a potential therapy to delay the onset or progression of one or more symptoms associated with muscular dystrophy, to accelerate the muscle repair of the subject suffering from muscular dystrophy, to improve muscular health and to accelerate repair process of muscles in other muscular disorders.

Athlete/construction worker-prevention: In some embodiments, the methods of increasing or maintaining muscle strength are provided to prevent muscle injury and/or loss, which would occur to a subject who participates in activities that might cause muscle injury or loss, such as, but not limited to an athlete, and construction workers.

General diseases: In some examples, GlcNAc, the related saccharides, or combinations thereof is administered to a subject suffering from muscle atrophy, muscle loss, muscle density loss, and muscle strength loss, such as, but not limited to, a subject at risk of acquiring or suffering from muscular dystrophy, to improve the subject's symptoms or prevent progress of his diseases.

Drug induced muscle toxicity: In some examples, GlcNAc, the related saccharides, or combinations thereof that induce the similar effect of GlcNAc on muscle or myogenesis is administered to a subject to prevent, treat, and delay the progression of muscle disorders such as, but not limited to, muscle atrophy, muscle injury, muscle wasting, muscle strength loss caused by the treatment with drugs, such as statins.

Post-surgery: In some examples, GlcNAc, the related saccharides, or combinations thereof that induce the similar effect of GlcNAc on muscle or myogenesis is administered to a subject before or after surgery, such as to a subject that has undergone surgery and may be at risk of muscle loss, muscle strength loss, or muscle density loss.

Cancer etc.: In some examples, GlcNAc, the related saccharides, or combinations thereof that induce the similar effect of GlcNAc on muscle or myogenesis is administered to a subject that has a risk of muscle loss, muscle wasting, and muscle atrophy caused by illnesses such as, but not limited to, cancer-associated cachexia, infection-induced cachexia (such as AIDS), or chronic obstructive pulmonary disease-associated cachexia.

Aging: In some examples, GlcNAc, the related saccharides, or combinations thereof that induce the similar effect of GlcNAc on muscle or myogenesis is administered for preventing, treating, or slowing the progression of a sign or symptom associated with aging.

Cardiovascular disease: In some examples, GlcNAc, the related saccharides, or combinations thereof that induce the similar effect of GlcNAc on muscle or myogenesis is administered a subject, who has at high risk of cardiovascular disease or who has cardiovascular disease to accelerate the repair of damaged cardiac muscle, improve the health of cardiac muscle, and increase the strength of cardiac muscle.

An advantage of the present application is to delay the onset or progression of muscle disorders and/or to counteract muscular dystrophy, muscle injury, muscle atrophy, and muscle loss.

A further advantage of the present application is to utilize commercially available products to treat muscle disorders.

Another advantage of the present application is that GlcNAc is shown not to have any significant adverse effect in human by long-term oral administration.

DESCRIPTION OF THE DRAWINGS

FIG. 1 is a graph illustrating the increase of myogenesis of mouse myoblasts with the addition of N-acetylglucosamine.

FIGS. 2A and 2B are digital images illustrating myotubes without and with the presence of N-acetylglucosamine, respectively.

FIG. 3 is a graph illustrating the increase of the myogenesis of human myoblasts obtained from a patient of myotonic dystrophy 1 with the addition of N-acetylglucosamine.

FIGS. 4A-4C and 4D-4F are digital images illustrating that exogenously added glucosamine fails to promote the myogenesis at the dose at which N-acetylglucosamine increases the formation of myotubes.

FIGS. 5A-5F are graphs illustrating that N-acetylglucosamine restores the myogenesis that is partially impaired by statin.

DETAILED DESCRIPTION OF THE INVENTION

Before the present compounds, compositions, and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

The term "administration" means to deliver therapeutically effective amounts of a compound or a compound with a pharmaceutical carrier and/or inactive components to a patient for prevention or treatment purpose. The method of administration includes, but is not limited to, injection, oral administration, sublingual administration, transdermal administration, and intranasal administration.

The term "disease" means any disease which can be treated by the preventive and the therapeutic methods with N-acetylglucosamine or N-acetylglucosamine with a pharmaceutical carrier and/or inactive components. Examples of such diseases include muscular dystrophy, muscular atrophy, muscular weakness, muscular injury, muscle wasting, muscle strength loss caused by the treatment with a drug which show muscular toxicity, cancer, and cardiovascular diseases.

The term "muscular dystrophy" refers a group of heterogeneous genetic muscular diseases, which are characterized by progressive degeneration and weakness of skeletal muscle. Myotonic dystrophy type 1 (DM1) is the most common form of muscular dystrophy developing in adulthood. DM1 is a multisystem disorder that affects the skeletal muscle, the smooth muscle, the eye, the heart, the endocrine system, and the central nervous system. The progressive muscle degeneration occurs and the myogenesis is generally impaired, which leads to the depletion of the satellite cells. DM1 is caused by expansion of a CTG trinucleotide repeat in the noncoding region DMPK (dystrophia myotonica protein kinase), which encodes an enzyme, a serine/threonine kinase. An expansion of this volatile repeat over 50 results in DM1 dystrophy symptoms having an increasing severity corresponding to an increasing numbers of repetitions. Muscle tissue of DM1 patients is histologically abnormal. Features include the variability in size of the fibers, fibrosis, rows of inner cores, annular fibers, sarcoplasmic masses, and an increase in intrafusal muscle fibers. In patients having DM1, the adult muscle regeneration is continuously activated due to frequent muscle injury, leading to deplete muscle stem cells. The most common form of muscular dystrophy in childhood with an incident of 1:5000 is Duchenne muscular dystrophy (DMD), a severe X-linked recessive disorder. Individuals affected with this dystrophy suffer from progressive muscle wasting and severe muscle degeneration, which becomes evident before the age of 4 years old, need assisted ventilation before the age of 20 years old, and have short lives. Their muscle lacks a protein called dystrophin, an essential linker that connects the intracellular cytoskeleton of myofibers to the extracellular matrix. Consequently, the muscle membrane does not tolerate repetitive contraction, which leads to progressive muscle degeneration.

The term "genetic predisposition" means that a subject has the higher risk to develop a disease due to a factor related to genetic information and/or modification of genetic information caused by epigenetic regulations.

The term "related saccharides" means groups of monosaccharides or oligosaccharides that contains N-acetylglucosamine residues or modified monosaccharides.

The term "effective amount" means the amount of N-acetylglucosamine or N-acetylglucosamine with a pharmaceutical carrier and/or inactive components, which generate a desired response to a subject.

The term "muscle" means a structure, which is composed of myoblasts, myotubes, myofibers, stem cells that could produce myoblasts, and proteins that support those structures. The muscle includes skeletal, cardiac, and smooth muscles.

The term "myogenesis" means a process that leads to produce muscle fibers. Myogenesis is generally composed the steps of the differentiation of myoblasts to myocytes, fusion of myocyte into myotubes, maturation of myotumes, and myofiber formation.

The term "cell matrix" means the extracellular structures, which is composed of proteins including collagen, fibronectin, laminin, and proteoglycans. Those proteins often attach to oligosaccharides, providing hydrophilic environment to cells.

The term "muscle environment" means an environment which surrounds myoblasts, myocytes, myotumes, and myofibers. An optimized muscle environment could be created by modification of proteins with certain types of oligosaccharides.

The term "glycosylation of proteins" means the modification of proteins with oligosaccharides. The oligosaccharides include, but are not limited to, N-linked complex type oligosaccharides, O-linked mucin type oligosaccharides, and O-linked mannosyl glycans.

The term "muscular health" refers the condition of muscle where a subject find any obvious inconvenience to carry out daily life.

The term "muscle injury" refers the condition that muscle does not functioning normally. The injury could be caused by excessive impact to a muscle where muscle fibers compressed in this manner can become irritated and even torn, caused when a muscle is stretched beyond its capacity and caused when intense and rapid contraction is demanded of a muscle.

The terms "muscle atrophy" and "muscle loss" refer the condition which is caused by disuse of muscles, e.g. a lack of physical activity. For example, a subject under the medical conditions that limit their movement can lose muscle tone and develop atrophy.

The term "muscle strength" means the amount of the force that muscle can produce with maximal efforts.

The term "cancer-associated cachexia" and "infection-induced cachexia" mean an ongoing loss of skeletal muscle mass that cannot be reversed by conventional nutritional support and leads to progressive functional impairment. Cachexia caused by cancer refers "cancer-associated cachexia" and induced by infection is defined as "infection-induced cachexia".

The term "aging" means the physiological process, which associates a progressive functional decline, or a gradual deterioration of physiological function with age.

The term "cardiovascular disease" refers to disease of the circulatory system including the heart and blood vessels. There are four main types of cardiovascular disease: coronary heart disease, stroke, peripheral arterial disease, and aortic disease.

The term "pharmaceutically acceptable carriers" means the pharmaceutically acceptable compositions and formulations suitable for pharmaceutical delivery of therapeutic agents.

The term "regeneration" means the repair of cells, tissues, or organs. In the present invention, the regeneration refers the repair of myoblasts, myofibers, and muscular environment, which could provide an optimal environment to generate myofibers.

The term "subject" means living multicellular vertebrate organisms, including but not limited humans, rats, mice, and other non-human mammals.

The term "treating disease" means the therapeutic intervention to improve symptoms of a disease. The term also refers to reversing or inhibiting symptoms or delaying progress of diseases or improving physiological condition. Treating disease does not require a total absence of diseases.

N-Actylglucosamine (GlcNAc) is a modified monosaccharide, an amino sugar, directly incorporated into oligosaccharides and glycosaminoglycans. The GlcNAc molecules having various substitutions of functional groups serve as decorative components of the cell surface where they can be directly involved in cellular interactions and in other cellular physiological activities including, but not limited to, cell growth and differentiation process. These carbohydrates can increase the specificity and strength of the interaction between cells as well as modulate physiological activities. GlcNAc provides a greater synthesis of N-linked oligosaccharide and O-linked oligosaccharide compared to glucose and glucosamine. In particular, approximately 90-100% of GlcNAc which is uptaken by cells is used for the synthesis of oligosaccharides attached to proteins, while about 1-10% of glucose or glucosamine that is uptaken by cells is used for the synthesis of oligosaccharides attached to glycoproteins.

A majority of the glucosamine or glucose in muscle tissue is metabolised by glycolysis pathway (converted into ATP) or used to produce glycogen. In contrast, GlcNAc is exclusively used to biosynthesize oligosaccharides. Further, pure GlcNAc is available as a supplement (food additive).

The present invention provides methods for promoting myogenesis by providing an effective amount of N-acetylglucosamine (GlcNAc), related saccharides, and combinations thereof. More precisely, related saccharides can be modified GlcNAc or monosaccharides or GlcNAc containing oligosaccharides. In some embodiments, the effective amount of GlcNAc may range from about 0.004 g/Kg body weight to about 0.37 g/Kg body weight per day. In a preferred embodiment, the effective amount of GlcNAc may range from about 0.002 g/Kg body weight to about 0.2 g/Kg body weight per day.

In some embodiments, GlcNAc promotes myogenesis of rodent myoblasts.

In some embodiments, GlcNAc promotes myogenesis of myoblasts derived from clinically normal individual.

In some embodiments, GlcNAc promotes myogenesis of myoblasts derived from DM1 patients.

In some embodiments, GlcNAc promotes myogenesis of myoblasts derived from DMD patients.

In some embodiments, the promotion of myogenesis was achieved by exposing myoblasts to the physiological concentration of GlcNAc. More precisely, the concentration is 0.1, 0.2, 0.5, 1, 2, 5, and 10 mM. Those concentrations of GlcNAc promote cell-cell interaction of myoblasts, leading to the promotion of myogenesis. The promotion results in the increased formation of myotubes with increased number of nuclei. In another embodiment, those concentrations of GlcNAc promote interaction of myoblasts with cell matrixes, promoting myogenesis by stabilizing the interaction of myotubes with cell matrixes.

In some embodiment, oral administration, intravenous injection or other relevant administration methods can be used to achieve the physiological concentration of GlcNAc in a subject.

In some embodiment, the promotion of myogenesis can be achieved by increasing the concentration of GlcNAc by oral administration, intravenous injection or other relevant administration methods.

In some embodiments, GlcNAc delays the progress of DMD of model mice and improve the functions of muscle of DMD mouse model. The GlcNAc may be orally or intraperitoneally administered.

In other embodiments, glucosamine, which is an analogue of GlcNAc and has been used as a dietary supplement for junction pain, showed toxicity to the myotubes, resulting in the inhibition of myogenesis. Thus, while glucosamine has similar chemical structure with GlcNAc, biological effect of glucosamine on myogenesis is distinct from that of GlcNAc.

In some embodiments, methods of treating muscular dystrophy patients are disclosed. In some embodiments, the method comprises administrating GlcNAc, the related saccharides, or combinations thereof to the subjects with muscular dystrophy an effected amount of GlcNAc, the related saccharides, or combinations thereof, which promotes the myogenesis of the subjects, thereby improving their symptoms, delaying progress of their diseases and increasing the chance of survival.

In some embodiments, methods of increasing or maintaining muscle strength are disclosed. In some embodiments, the method comprises administrating GlcNAc, the related saccharides, or combinations thereof to the subjects who have higher risk to injure their muscles. The subject could be athletes or workers who use their muscle more significantly than other workers. More precisely, the worker could be construction workers, movers and mine workers. Administration of GlcNAc, the related saccharides, or combinations thereof could improve the regeneration of the subjects' muscles or prevent the muscular injury caused by the use of their muscles.

In some embodiments, methods of treating to or reducing the risk of muscle loss caused by wasting and/or atrophy are disclosed. In some examples, GlcNAc, the related saccharides, or combinations thereof is administered to a subject at risk of muscular loss or injury, such as a subject with a risk of suffering from or acquiring a condition or diseases associated with muscle loss, wasting and atrophy.

In some embodiments, methods of treating, preventing or delaying the progression of muscle disorders such as, but not limited to, muscle atrophy, muscle injury, muscle wasting, and muscle strength loss caused by the treatment with drugs are disclosed. In some examples, GlcNAc, the related saccharides, or combinations thereof is administered to a subject who are under the medication of a drug, which could have a side effect to induce muscle atrophy, muscle injury, muscle wasting, and/or muscle strength loss. More precisely, the drugs could be blood cholesterol-lowering drugs, statins, such as Atorvastatin or Simvastatin.

In some embodiments, methods of maintaining or increasing muscle health of subject, who will have or had a surgical operation are disclosed. In some examples, GlcNAc, the related saccharides, or combinations thereof, could be administered to a subject prior or after surgical operation, which could cause muscular damage, thereby promoting recovery of the subject from the surgical operation.

In some embodiments, methods of counteracting muscle loss, muscle wasting, and muscle atrophy caused by such as but not limited to cancer-associated cachexia, infection-induced cachexia (such as AIDS), or chronic obstructive pulmonary disease-associated cachexia, are disclosed. In some examples, GlcNAc, the related saccharides, or combinations thereof, could be administered to a subject who are suffering cachexia to improve their symptoms.

In some embodiments, methods of preventing, treating or slowing the progression of a sign or symptom associated with aging. In some examples, GlcNAc, the related saccharides, or combinations thereof that induce the similar effect of GlcNAc on muscle or myogenesis is administered to a subject who are suffering age related muscular problems.

In one embodiment of the present application, the method of treating a muscle disorder includes the step of providing a dose of GlcNAc having a concentration of 2 mM=442 mg/L of less than 50 mg/kg BW per day, amounting to about 3 g/d for a person who weighs 60 kg.

In some embodiments, methods of preventing cardiovascular disorders or treating cardiovascular disease is disclosed. In some examples, GlcNAc, the related saccharides, or combinations thereof that induce the similar effect of GlcNAc on muscle or myogenesis that induce the similar effect of GlcNAc on muscle or myogenesis is administered to a subject, who has at high risk of cardiovascular disease or who has cardiovascular disease to accelerate the repair of damaged cardiac muscle, improve the health of cardiac muscle and increase the strength of cardiac muscle.

EXAMPLES

Example 1: Rodent Myoblasts

N-Acetylglucosamine promotes myogenesis of murine myoblasts: Myogenesis of murine myoblast cells, C2C12 cells was induced by replacing the medium from growing medium (DMEM supplemented with 10% fetal calf serum) to DMEM supplemented with 1% horse serum, insulin (10 µg/ml), transferrin (5.5 µg/ml) and selenium (5 ng/ml) in the presence or absence of different doses of N-acetylglucosamine (GlcNAc). This condition induces the differentiation of myoblasts, including the induction of the synthesis of myosine heavy chains (MHC). Then myoblasts start fusing with each other to form myotubes, which are multinucleated. Cells were fixed in 3.8% paraformaldehyde containing phosphate buffered saline (PBS) for 15 min. Then cells were permeabilized by PBS-0.25% Triton X100 for 5 min. After washed with PBS, the cells were incubated with anti-MHC antibody (Clone MF-20, 2.5 µg/ml) in the blocking agents (Vectors laboratories) for an hour, followed by anti-mouse antibody labelled with Alex 488. Then nuclei of the cells were stained with DAPI. Fluorescent images were taken through 20× objectives by using Queorum WaveFX spinning Disc confocal system.

In the condition shown in FIG. 1, the myogenesis was stopped after the differentiation for 72 hours, which was 18 hours after the presence of myotubes became detectable. The result shows that GlcNAc increases the number of multinuclear MHC expressing myotubes, demonstrating that GlcNAc promotes myogenesis of C2C12 cells even at the dose of 0.2 mM. In FIGS. 2A and 2B, the differentiation was stopped at 62 hours. Fields of view (5×5 FOVs) are stitched together and shown here. One FOV is 0.533 mm square. White color is MHC-positive myotube cells. A comparison of FIGS. 2A and 2B suggests that GlcNAc increased not only the number of multinuclear MHC expressing myotubes but also the length and width of the myotubes, clearly indicating its capacity to facilitate the myogenesis.

Example 2: Human Myoblasts

GlcNAc Promotes the Myogenesis of Myoblasts Derived from a Patient of Myotonic Dystrophy 1:

It is known that myogenesis is impaired in myotonic dystrophy 1 (DM1). The therapeutic potential of GlcNAc on this impaired myogenesis was thus tested. Myoblasts derived from a patient of DM1 were grown in DMEM supplemented with 20% fetal calf serum till the density of cells reached to 90% confluency. Then, the differentiation was induced by changing the medium to DMEM supplemented with 1% fetal calf serum, 10 µg/ml insulin, and 100 µg/ml apotransferrin. After 120 hours, cells were fixed and MHC in the cells were visualized by the method described in Example 1. FIG. 3 shows that GlcNAc promote the myogenesis of human myoblasts of DM1, indicating that treatment of GlcNAc can rescue the impaired myogenesis that occurs in DM1 patients.

Example 3: Glucosamine Vs GlcNAc

GlcNAc but not its Derivative Glucosamine Promotes the Myogenesis (FIGS. 4A-4F):

Glucosamine is a commercially available supplement, which has been claimed to reduce arthritic pain, although there is any scientific evidence to support this claim. It was examined whether glucosamine has any significant effect on the myogenesis. Myogenesis of murine myoblast cells, C2C12 cells was induced by replacing the medium from growing medium (DMEM supplemented with 10% fetal calf serum) to DMEM supplemented with 1% horse serum, insulin (10 µg/ml), transferrin (5.5 µg/ml) and selenium (5 ng/ml) in the presence or absence of different doses of N-acetylglucosamine (GlcNAc) or glucosamine. This condition induces the differentiation of myoblasts, including the induction of the synthesis of myosine heavy chains (MHC). Then myoblasts start fusing each other to form myotubes, which are multinucleated. Cells were fixed in 3.8% paraformaldehyde containing phosphate buffered saline (PBS) for 15 min. Then cells were permeabilized by PBS—0.25% Triton X100 for 5 min. After washed with PBS, the cells were incubated with anti-MHC antibody (Clone MF-20, 2.5 µg/ml) in the blocking agents (Vectors laboratories) for an hour, followed by anti-mouse antibody labelled with Alex 488. Then nuclei of the cells were stained with DAPI. Fluorescent images were taken through 20× objectives by using Queorum WaveFX spinning Disc confocal system. FIG. 4 shows that unlike GlcNAc, glucosamine induce cell toxicity and fails to induce any positive impact on the myogenesis. Thus, this data suggests the specificity of GlcNAc on the positive influence on the myogenesis.

Example 4: Statin

GlcNAc Reduces Statin-Induced Reduction in Myogenesis (FIGS. 5A-5F):

It is estimated that 10-15% of individuals who take statins-related compounds develop statin-related muscle adverse effects, ranging from mild myalgia to more severed muscle symptoms while the mechanism of statin-induced myopathy remains undetermined. In vitro myogenesis, statins-related compounds reduce in vitro myogenesis and stable adhesion of myotubes. Thus, it was examined whether GlcNAc treatment has any significant effect on the statin-reduced myogenesis. Myogenesis of murine myoblast cells, C2C12 cells was induced by replacing the medium from growing medium to differentiation medium as above DMEM in the presence or absence of different doses of N-acetylglucosamine (GlcNAc) with or without Simvastatin for 44 hours. Cells were then fixed in 3.8% paraformaldehyde containing phosphate buffered saline (PBS) for 15 min. Then cells were permeabilized by PBS-0.25% Triton X100 for 5 min. After washed with PBS, the cells were incubated with anti-MHC antibody (Clone MF-20, 2.5 µg/ml) in the blocking agents (Vectors laboratories) for an hour, followed by anti-mouse antibody labelled with Alex 488. Then nuclei of the cells were stained with DAPI. Fluorescent images were taken through 20× objectives by using Queorum WaveFX spinning Disc confocal system. In the presence of Simvastatin, the formation of myotube was reduced and the differentiated myotube appeared to be fragile and did not adhere tightly to the dish. FIG. 5 and other preliminary data show that GlcNAc treatment stabilizes the adhesion of myotubes (data not shown) and renders myoblast appropriate differentiation even in the presence of Simvastatin.

It should be noted that various changes and modifications to the presently preferred embodiments described herein will be apparent to those skilled in the art. Such changes and modifications may be made without departing from the spirit and scope of the present invention and without diminishing its attendant advantages.

We claim:

1. A method of improving myogenesis in a subject in need thereof, comprising administering an effective amount of N-acetylglucosamine (GlcNAc) to the subject, thereby delaying the weakening of or improving the strengthening of muscles in the subject, wherein the subject has or is at risk of acquiring a muscular dystrophy.

2. The method of claim 1, wherein the method includes administering GlcNAc to a subject prior to a surgical procedure, following a surgical procedure, or both.

3. The method of claim 1, wherein the subject is at risk of muscle injury, muscle loss, or combinations thereof.

4. The method of claim 1, wherein the subject has or is at risk of acquiring Myotonic dystrophy.

5. The method of claim 1, wherein the subject has or is at risk of acquiring Duchenne muscular dystrophy.

6. A method of improving myogenesis in a subject in need thereof, comprising administering an effective amount of N-acetylglucosamine (GlcNAc) to the subject, thereby delaying the weakening of or improving the strengthening of muscles in the subject, wherein the subject suffers from cancer associated cachexia, infection-induced cachexia, chronic obstructive pulmonary diseases-associated cachexia, or combinations thereof.

7. A method of improving myogenesis in a subject in need thereof, comprising administering an effective amount of N-acetylglucosamine (GlcNAc) to the subject, thereby delaying the weakening of or improving the strengthening of muscles in the subject, wherein the subject has a cardiovascular disease.

* * * * *